US00PP08503P

United States Patent [19]

McGredy

[11] Patent Number: Plant 8,503

[45] Date of Patent: Dec. 21, 1993

[54] MINIATURE ROSE PLANT NAMED 'MACPLUTO'

[76] Inventor: Samuel D. McGredy, 130 B Beach Road, Caster Bay, Auckland 9, New Zealand

[21] Appl. No.: 628,608

[22] Filed: Dec. 17, 1990

[51] Int. Cl.[5] ..... A01H 5/00

[52] U.S. Cl. ..... Plt./7.1

[58] Field of Search ..... Plt. 7, 7.1, 22, 12, Plt./11

[56] References Cited

U.S. PATENT DOCUMENTS

P.P. 4,029 3/1977 Moore ..... Plt. 7.1

P.P. 4,867 7/1982 Moore ..... Plt. 7

P.P. 5,328 11/1984 Moore ..... Plt. 7

*Primary Examiner*—Howard J. Locker

[57] ABSTRACT

The present invention relates to a new and distinct variety of rose plant of the miniature rose class which was originated by crossing as seed parent the cultivar 'Matangi' and as pollen parent the cultivar 'Stars 'n Stripes' (U.S. Plant Pat. No. 4,029). It is a new, almost continuously and profusely blooming rose plant, of the miniature class, having well formed buds with hybrid tea shape and open-faced flowers with petals slightly cupped and reflexing, with contrasting red and white stripes. The flowers are pleasantly highlighted by their placement over a healthy and dense crop of glossy, deep green foliage on an upright and vigorously growing, well branched plant.

1 Drawing Sheet

BACKGROUND OF THE INVENTION

The present invention relates to a new and distinct variety of rose plant of the miniature rose class which was originated by me by crossing, as the seed parent, the rose known as 'Matangi' and as pollen parent the rose plant known as 'Stars 'n Stripes' (U.S. Plant Pat. No. 4,029). Upon recognition of the attributes of this plant within the progeny of the stated cross, it was selected for further testing and observation. Upon recognition that this plant was novel and expressed numerous superior and desirable traits as described below, the plant of this application was assigned an international recognition name of 'Macpluto'. This plant has been asexually reproduced by me or under my direction by cuttings and by budding in Washington County, Oreg. Such asexual reproduction has conclusively shown that all distinguishing characteristics of this plant come true to form, are firmly fixed, and are faithfully transmitted through succeeding propagations.

Specimens described below were grown in Washington County, Oreg.

SUMMARY OF THE INVENTION

The new plant of this invention contains a number of outstanding attributes in combination which set it apart from all other plants of the miniature rose market class. Such characteristics may be summarized as follows:

- A new and conspicuously attractive flower having red and white striped petals.
- Bud form similar to that typical of hybrid teas.
- Open-faced flowers which open to a substantially flat form with petals slightly cupped and reflexing, set off in full bloom by golden yellow stamens.
- Petals of gently rounded shape and of pleasing characteristicly contrasting and random patterns of red and white stripes.
- A plant which is highly remontant and blooms almost continuously and profusely.
- Flowers formed singly or in sprays of 3 to 5 placed over a healthy and dense crop of glossy, deep green foliage on an upright, compact, but vigorously growing, and well branched plant.

BRIEF DESCRIPTION OF THE DRAWING

The single sheet of photographic drawing depicts the buds and open-faced flowers of 'Macpluto' in various stages of maturity; the flower stems of the plant, and the vegetative growth and foliage characteristics of the plant in colors as true as is reasonably possible to attain in a color illustration of this nature.

Color terminology used in the descriptions which follow is in accordance with the Royal Horticultural Society Colour Chart (RHSCC). The terminology used in the color descriptions herein refers to plate numbers in the aforementioned color chart.

BOTANICAL DESCRIPTION OF THE PLANT

The following botanical descriptions are based on specimens of the plant as observed growing out doors in Washington County, Oreg., during the month of July.

Parentage:

*Seed parent.*—'Matangi'.

*Pollen parent.*—'Stars 'n Stripes' (U.S. Plant Pat. No. 4,029).

Classification: Miniature.

FLOWER

Blooming habit: Nearly continuous, with blooms occurring both singly and in clusters of normally about 3 to 5.

A. Buds:

(1) *Size.*—About 2½ cm. long.

(2) *Form.*—Pointed.

(3) *Color.*—A white bud showing red stripes near RHS 47A.

(4) *Sepals.*—Permanent, spear-shaped, reflex with flower opening.

(5) *Peduncle.*—Length: About 2 cm. Aspect: Straight, erect. Color: Green (near RHS 136B).

B. Bloom:

(1) *Size.*—About 4½ cm. in diameter when fully expanded.

(2) *Borne.*—Singly and in sprays of normally around 3 to 5.

(3) *Form.*—Initially slightly cupped, progressively becomes flat with advanced opening; slight relexing of the petals.

(4) *Petalage.*—About 28 under normal conditions.

(5) *Color.*—White (RHS 155D) with many variegations and striping of red tones beginning with RHS 47A and turning to RHS 53A with age.

C. Petals:

(1) *Texture.*—Moderately thick and of good substance.

(2) *Appearance.*—Velvety inside, velvety outside.

(3) *Form.*'Round, smooth edged and reflexing when bloom is fully opened.

(4) *Arrangement.*—Regularly arranged to form substantially semidouble flowers.

(5) *Petaloids in center.*—Medium, surrounding center, generally much smaller than and of the same coloration as petals.

(6) *Persistence.*—Petals drop off cleanly.

(7) *Fragrance.*—Moderate.

(8) *Lasting quality.*—Long lasting, usually around 7 days on the plant or as a cut flower.

REPRODUCTIVE ORGANS

A. Stamens, filaments and anthers:

(1) *Arrangement.*—Regularly arranged around and superior of pistils. Flower center is plainly visible in fully opened flower.

(2) *Color.*—Medium yellow.

B. Pollen: Color is medium yellow.

C. Styles: Even length; introrse.

D. Stigmas: Color is medium yellow.

E. Hips: Present; develop to about ¾ cm. diameter.

PLANT

A. Form: Tall and upright.

B. Growth: Vigorous.

C. Foliage:

(1) *Character.*—Normally compound 7 leaflet leaves with 5 leaflet leaves sometimes below the bloom.

(2) *Leaflet size.*—Average about 2 cm. in length.

(3) *Quantity.*—Abundant.

(4) *Color.*—New foliage is green (RHS 135C) maturing to RHS 139A.

(5) *Shape.*—Oval pointed, supported by short petiolule.

(6) *Texture.*—Glossy.

(7) *Margin.*—Serrated.

(8) *Serrations.*—Small and shaped like saw teeth.

(9) *Leaf stem.*—Color is RHS 135C turning to RHS 139B.

(10) *Stipules.*—Slightly bearded, and about ½ cm. long.

(11) *Rachis.*—Upper side grooved with a V-shaped center; about 1 cm. long; medium green in coloration.

(12) *Resistance to disease.*—Blackspot: Average. Mildew: Average. Rust: Average.

D. Wood:

(1) *New wood.*—Color is light green (about RHS 136B); smooth bark.

(2) *Old wood.*—Sturdy; color is green (about RHS 138B) with smooth bark; about 3 cm. internode spacing.

E. Thorns:

(1) *Quantity.*—Average on main stalk and on laterals.

(2) *Form.*—Dilated at base and declining.

(3) *Length.*—About ⅓ cm.

(4) *Color.*—Rose, turning brown at maturity.

(5) *Position.*—Ordinary.

F. Prickles: Average.

G. Winter hardiness: Requires ordinary protection in extreme climates.

I claim:

1. A new and distinct variety of miniature rose plant substantially as herein described and illustrated, which is particularly characterized by being of tall, hardy, upright, and much branched habit, with blooms borne singly or in sprays of 3 to 5, and the petals slightly reflexing with the mature bloom showing golden yellow stamens, and resembling in form, but with more intense coloration, the bloom of its pollen parent, 'Stars 'n Stripes' (U.S. Plant Pat. No. 4,029).

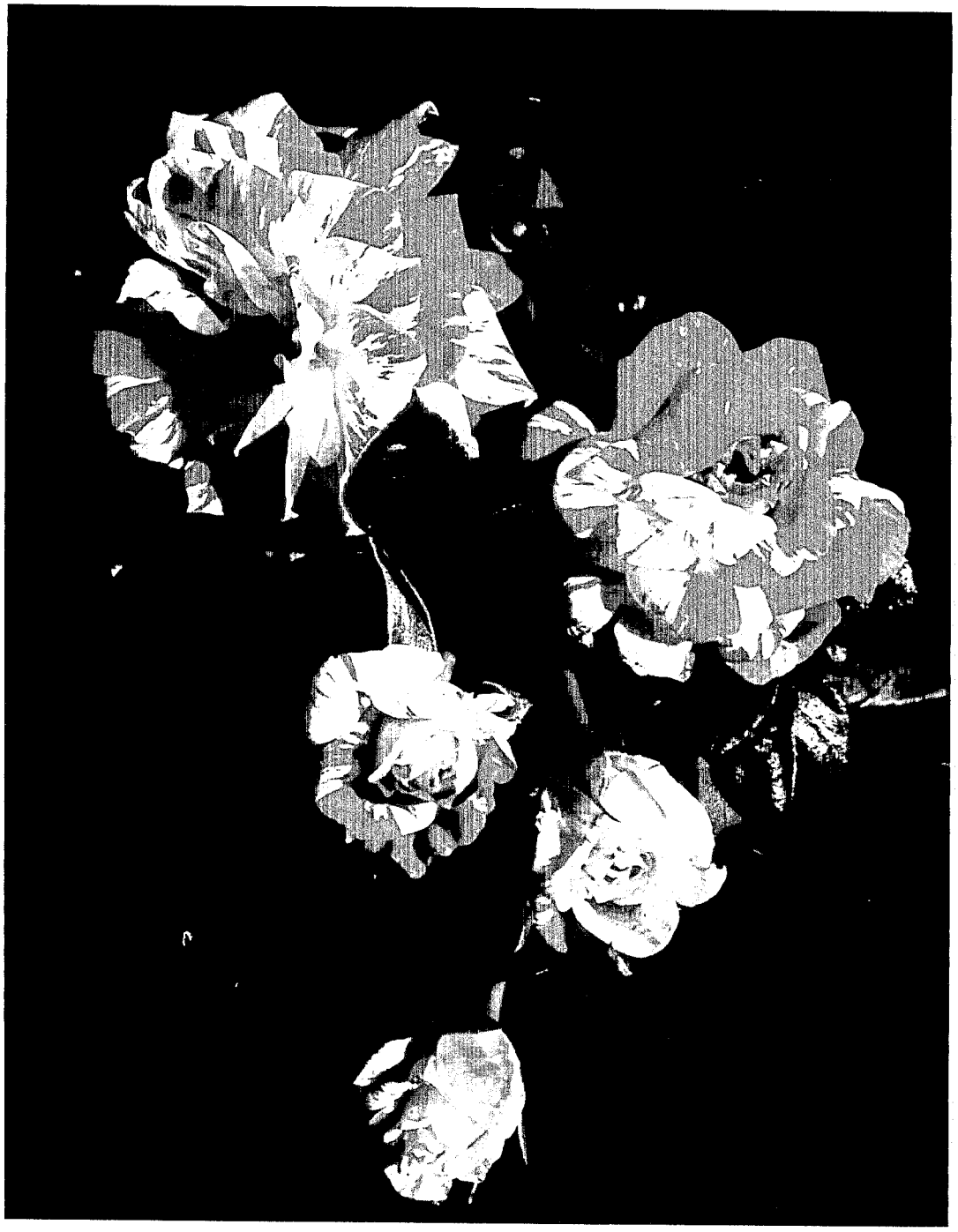

* * * * *